United States Patent [19]
Ballou et al.

[11] Patent Number: 5,735,275
[45] Date of Patent: Apr. 7, 1998

[54] TONOMETER UTILIZING HYDRAULIC PRESSURE

[76] Inventors: Jon Ballou, 54 Ellsworth Ave., Beverly, Mass. 01915; Francis J. Porter, 7 King Philip Dr., Millis, Mass. 02054; August O. Westner, 5 Wright St., Winchester, Mass. 01890

[21] Appl. No.: 661,794

[22] Filed: Jun. 13, 1996

[51] Int. Cl.⁶ ................................................. A61B 3/16
[52] U.S. Cl. ............................................ 128/645; 128/650
[58] Field of Search ........................ 128/645–652, 128/774; 73/78, 81

[56] References Cited

U.S. PATENT DOCUMENTS

| | | | |
|---|---|---|---|
| 1,419,134 | 6/1922 | Goldstein | 128/650 |
| 3,070,087 | 12/1962 | Sittel | 128/649 |
| 3,832,891 | 9/1974 | Stuckey | 73/80 |
| 4,221,567 | 9/1980 | Clark et al. | 23/230 B |
| 4,599,353 | 7/1986 | Bito | 514/530 |
| 4,786,394 | 11/1988 | Enzer et al. | 204/401 |
| 4,951,671 | 8/1990 | Coan | 128/652 |
| 4,965,253 | 10/1990 | Goldberg et al. | 514/54 |
| 5,002,057 | 3/1991 | Brady | 128/652 |
| 5,031,622 | 7/1991 | LaHaye | 128/646 |
| 5,113,863 | 5/1992 | Herman | 128/652 |
| 5,165,409 | 11/1992 | Coan | 128/652 |
| 5,174,290 | 12/1992 | Fiddian-Green | 128/632 |
| 5,176,143 | 1/1993 | Eckerle et al. | 128/677 |
| 5,186,172 | 2/1993 | Fiddian-Green | 128/632 |
| 5,241,964 | 9/1993 | McQuilkin | 128/672 |
| 5,271,405 | 12/1993 | Boyer et al. | 128/672 |
| 5,318,029 | 6/1994 | Palese | 128/652 |
| 5,343,861 | 9/1994 | Herman | 128/652 |
| 5,349,955 | 9/1994 | Suzuki | 128/645 |
| 5,415,165 | 5/1995 | Fiddian-Green | 128/632 |
| 5,540,227 | 7/1996 | Poole | 128/652 |

*Primary Examiner*—Jennifer Bahr
*Assistant Examiner*—Bryan K. Yarnell
*Attorney, Agent, or Firm*—Testa, Hurwitz & Thibeault, LLP

[57] ABSTRACT

A tonometer for measuring intraocular pressure of an eye is described. The tonometer includes an eyepiece having a conduit extending through an outer surface. The outer surface is concave shaped to conform to an eyeball. The tonometer also includes a plunger extending through the conduit having a head at a first end and having a probe at a second end which extends beyond the outer surface of the eyepiece so as to contact the eyeball when the eyepiece is positioned to conform to the eyeball. The tonometer also includes a fluid reservoir having a top and a bottom. The bottom of the reservoir is sealed by a membrane that is in juxtaposition with the head of the plunger. In addition, the tonometer includes an indicator positioned in the fluid reservoir for measuring a level of fluid in the reservoir. The level of fluid in the reservoir is proportional to an intraocular pressure of the eyeball when the eyepiece is positioned to conform to the eyeball.

17 Claims, 1 Drawing Sheet

TONOMETER UTILIZING HYDRAULIC PRESSURE

FIELD OF THE INVENTION

The invention relates generally to the field of tonometers for measuring intraocular pressure of an eyeball. In particular, the invention relates to a hydraulic pressure tonometer which measures intraocular pressure by a fluid displacement technique and to methods of operating such a tonometer.

BACKGROUND OF THE INVENTION

Glaucoma is a disease that causes an abnormally high intraocular pressure which may result in severe and permanent vision loss. The high intraocular pressure caused by glaucoma slowly damages the optic nerve of the eye and will eventually result in total blindness if untreated. Glaucoma affects 2 % of the U.S. population over age 40. Fifteen percent of all cases of blindness in the U.S. is a direct result of glaucoma. Glaucoma is preventable if detected early enough. Unfortunately, glaucoma usually does not manifest symptoms until the optic nerve is permanently damaged.

Some individual are at a high risk of contracting glaucoma because of numerous factors such as heredity, injury or eye disease. Rapid detection of abnormal intraocular pressure is essential to preventing blindness in these high risk individuals. It is, however, not practical for most high risk glaucoma patients to have their intraocular pressure measured at daily or even weekly intervals.

The intraocular pressure of a human eye is usually determined through the use of a tonometer. A common type of tonometer is the applanation tonometer which determines intraocular pressure as a function of corneal flattening. Measurements are achieved by bringing the tip of the tonometer into contact with the outer surface of the cornea and measuring the intraocular pressure as the surface of the cornea is flattened.

When the surface of the cornea is flattened to a predetermined point, the pressure is noted.

Other tonometers measure intraocular pressure by utilizing a mechanical spring-loaded pressure means to apply pressure to the eyelid or eyeball. A resulting load applied to the pressure means is detected by a load sensor and is used to calculate intraocular pressure of the eye.

Prior art tonometers are typically operated by physicians or skilled medical technicians in a medical facility. The cost of providing very frequent measurements of intraocular pressure to all high risk patients would be a significant burden to the health care industry.

In addition, most prior art tonometers are subject to contamination. If one patient has a cornea which is contaminated with bacteria, and the lens of the tonometer tip is not adequately cleaned between use of the tonometer on succeeding patients, transmittal of the bacteria from one patient to a succeeding patients will likely occur. The problem of adequately cleaning and sterilizing the lens of the tonometer tip between usage of the tonometer is demanding and is often inadequately performed. It is not uncommon for a patient having recently undergone a tonometer test to develop "red eye", a bacterial and/or viral infection transmitted via the tonometer tip lens.

Moreover, prior art tonometers are typically not compact and portable. As a result, many communities, especially in lesser developed countries, do not have access to these instruments.

SUMMARY OF THE INVENTION

It is therefore a principal object of this invention to provide a compact, portable, inexpensive and easy to use tonometer that allows patients to frequently self-monitor their intraocular pressure. It is another object of this invention to provide a sterile tonometer that eliminates the spread of bacteria from one patient to another. It is another object of this invention to provide a tonometer that can be used with the eyelid closed. It is another object of this invention to provide a tonometer that generates a permanent record of the intraocular pressure measurement of the eye.

Accordingly, the present invention features a tonometer comprising an eyepiece having a conduit extending through an outer surface. The outer surface of the eyepiece is concave shaped to conform to an eyeball. A plunger extends through the conduit having a head at a first end and having a probe at a second end. The probe extends beyond the outer surface of the eyepiece and contacts the eyeball when the eyepiece is positioned to conform to the eyeball.

The tonometer also includes a fluid reservoir having a top and a bottom. The bottom of the reservoir is sealed by a membrane that is in juxtaposition with the head of the plunger. The top of the reservoir may be sealed by a breakable membrane. The reservoir may include an o-ring for sealing the bottom of the reservoir with the membrane. The reservoir may include a plug for filling the reservoir with a fluid. The fluid may be a mineral oil or a gauge oil.

A body is coupled to the eyepiece for housing the membrane and reservoir. An indicator is positioned in the fluid reservoir for measuring a level of fluid in the reservoir. The indicator may be insertable into the breakable membrane positioned at the top of the reservoir. The level of fluid in the reservoir is proportional to an intraocular pressure of the eyeball when the eyepiece is positioned to conform to the eyeball.

The present invention also features a method of measuring intraocular pressure of an eyeball. The method includes contacting the eyeball with an eyepiece having a plunger extending through the eyepiece. The step of contacting the eyeball with an eyepiece may be performed with the eyelid of the eyeball closed. Having the eyelid closed during a measurement is significantly more comfortable for the patient. The method also includes displacing the plunger a distance proportional to the force exerted on the plunger caused by contacting the eyeball to the eyepiece. This force is proportional to the intraocular pressure of the eyeball.

The method also includes displacing an amount of fluid proportional to the displacement of the plunger caused by contacting the eyeball to the eyepiece and thus proportional to the intraocular pressure of the eyeball. Displacing the amount of fluid proportional to the displacement of the plunger may be accomplished by displacing a membrane sealing the fluid reservoir.

In addition, the method includes measuring the fluid displacement caused by contacting the eyeball to the eyepiece. This fluid displacement measurement is proportional to the intraocular pressure of the eyeball. The method may include inserting an indicator into the fluid reservoir to measure the fluid displacement. The indicator may be permanently marked by the displaced fluid. The displaced fluid level may be calibrated to the intraocular pressure of the eyeball.

BRIEF DESCRIPTION OF THE DRAWINGS

This invention is described with particularity in the appended claims. The above and further advantages of this

Figure 1:
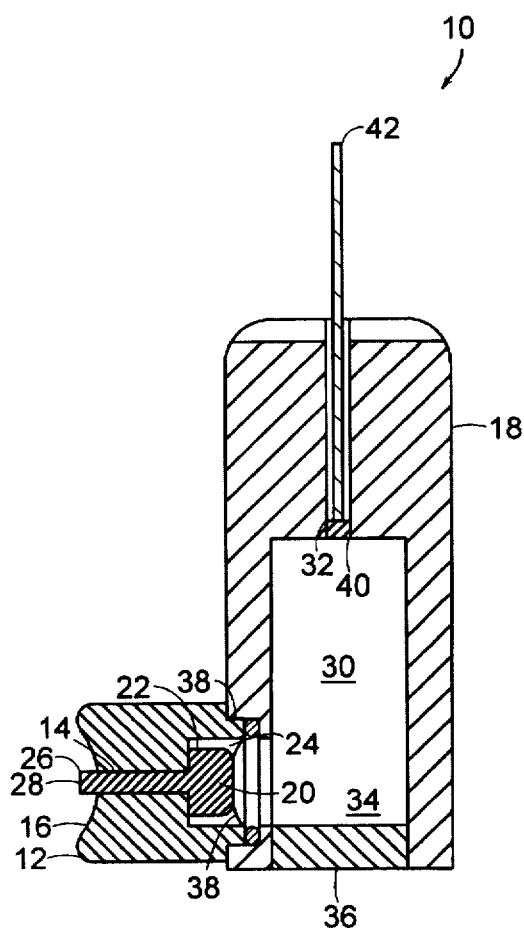

3 invention may be better understood by referring to the following description taken in conjunction with the accompanying drawings, in which:

FIG. 1 illustrates a cross-sectional view of tonometer that utilizes hydraulic pressure which embodies the invention.

Figure 2:
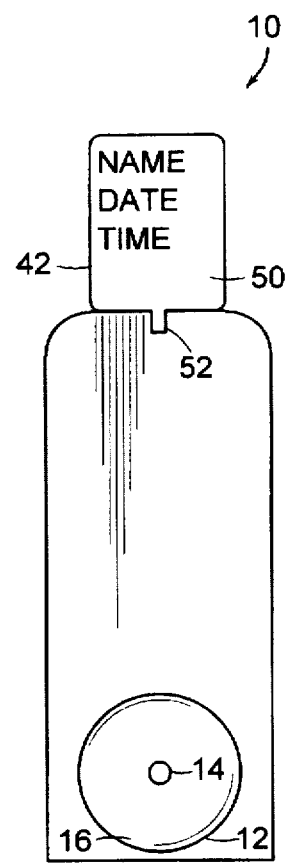

FIG. 2 illustrates a front view of tonometer that utilizes hydraulic pressure which embodies the invention.

Figure 3:
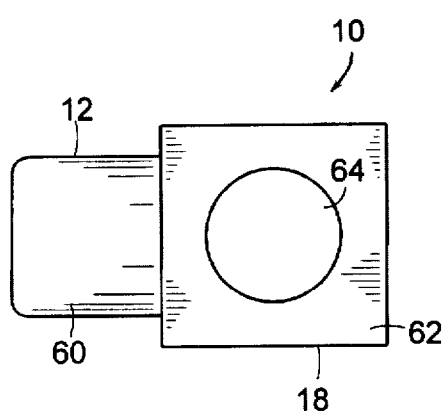

FIG. 3 illustrates a bottom view of tonometer that utilizes hydraulic pressure which embodies the invention.

Figure 4:
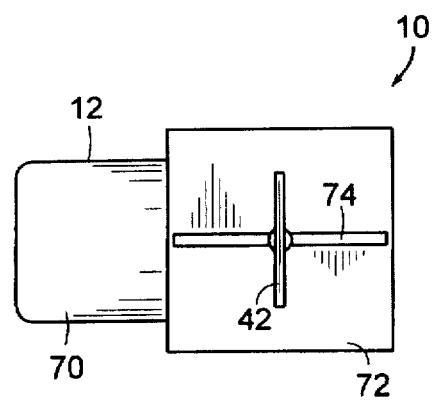

FIG. 4 illustrates a top view of tonometer that utilizes hydraulic pressure which embodies the invention.

DETAILED DESCRIPTION

FIG. 1 illustrates a cross-sectional view of a tonometer 10 that utilizes hydraulic pressure which embodies the invention. The tonometer 10 comprises an eyepiece 12 having a conduit 14 extending through an outer surface 16. The outer surface 16 of the eyepiece 12 is concave shaped to conform to an eyeball (not shown). The tonometer also includes a body 18 coupled to the eyepiece 12. The eyepiece 12 and the body 18 may be formed from injection molded plastic (e.g., ABS plastic) which is inexpensive, easy to control and non-absorbing.

The tonometer 10 also includes a plunger 20 extending through the conduit 14. The plunger 20 has a head 22 at a first end 24 and a probe 26 at a second end 28 which extends beyond the outer surface 16 of the eyepiece 12 so as to contact the eyeball when the eyepiece 12 is positioned to conform to the eyeball. The plunger 20 may also be formed from injection molded plastic or a metal such as aluminum.

The tonometer 10 also includes a fluid reservoir 30 within the body 18. The fluid reservoir 30 has a top 32 and a bottom 34. The fluid reservoir 30 must be large enough so that the intraocular pressure measurement is not too sensitive to modest changes in the angle at which the tonometer 10 may be held during measurement. The reservoir 30 may include a plug 36 for filling the reservoir 30 with a fluid.

The bottom 34 of the reservoir 30 is sealed by a flexible membrane 38 or thin diaphragm that is in close juxtaposition with the head 22 of the plunger 20. The membrane 38 may be formed of cellophane that is approximately 1 mil thick. The reservoir 30 may include an o-ring 38 for sealing the bottom 34 of the reservoir 30 with the membrane 38. The top 32 of the reservoir 30 may be sealed by a breakable membrane 40 that allows an indicator 42 to be inserted into the reservoir 30.

A fluid is contained within the fluid reservoir 30. The fluid typically has a well controlled density. Also, the fluid should have a low evaporation rate. In addition, the fluid should be relatively inert and non-absorbing to water vapor. The fluid may be mineral oil or a gauge oil.

The tonometer 10 also includes an indicator 42 positioned in the fluid reservoir 30 for measuring a level of fluid in the reservoir 30. The indicator 30 may be insertable into the breakable membrane 40 positioned at the top 32 of the reservoir 30. The indicator 42 typically is formed of a material that does not absorb the fluid to improve the repeatability of the measurement. The indicator 42 may be formed from injection molded plastic.

The indicator 42 marks the level in which the fluid reaches during an intraocular pressure measurement. The level of fluid in the reservoir 30 is proportional to an intraocular pressure of the eyeball when the eyepiece 12 is positioned to conform to the eyeball. The indicator 42 may be color-coded or otherwise marked to indicate whether the patent's intraocular pressure is normal, elevated, or abnormally high and requiring immediate notification of a physician.

FIG. 2 illustrates a front view of tonometer 10 that utilizes hydraulic pressure which embodies the invention. The eyepiece 12 and the conduit 14 extending through the outer surface 16 is shown. In addition, the front view illustrates a tab at a top 52 of the indicator 42. The tab 50 of the indicator 42 may have a label indicating the patient's name, the date and time of the measurement. The indicator 42 thus may be a permanent record which can be presented to the patient's physician.

FIG. 3 illustrates a bottom view of tonometer 10 that utilizes hydraulic pressure which embodies the invention. A bottom 60 of the eyepiece 12 and a bottom 62 of the body 18 is shown. In addition, a plug 64 for filling the fluid reservoir 30 (FIG. 1) is shown.

FIG. 4 illustrates a top view of tonometer 10 that utilizes hydraulic pressure which embodies the invention. A top 70 of the eyepiece 12 and a top 72 of the body 18 is shown. In addition, a slot 74 in which the indicator 42 is inserted into the fluid reservoir 30 (FIG. 1) is shown.

The tonometer 10 illustrated by FIGS. 1–4 is compact and inexpensive to manufacture. The body 18, eyepiece 12, plunger 20 and indicator 42 may be formed from inexpensive injection molded plastic. The eyepiece 12 and plunger 20 are typically sterilized prior to packaging. The entire tonometer 10 may sealed in an antiseptic package so that it remains sterile prior to use.

The present invention also features a method of measuring intraocular pressure of an eyeball. The method includes contacting the eyeball with an eyepiece having a plunger extending through the eyepiece. The step of contacting the eyeball with an eyepiece may be performed with the eyelid of the eyeball closed. Having the eyelid closed during a measurement is significantly more comfortable for the patient. The method also includes displacing the plunger a distance proportional to the force exerted on the plunger caused by contacting the eyeball to the eyepiece. This force is proportional to the intraocular pressure of the eyeball.

The method also includes displacing an amount of fluid proportional to the displacement of the plunger caused by contacting the eyeball to the eyepiece and thus proportional to the intraocular pressure of the eyeball. Displacing the amount of fluid proportional to the displacement of the plunger may be accomplished by displacing a membrane sealing the fluid reservoir.

In addition, the method includes measuring the fluid displacement caused by contacting the eyeball to the eyepiece. This fluid displacement measurement is proportional to the intraocular pressure of the eyeball. The method may include inserting an indicator into the fluid reservoir to measure the fluid displacement. The indicator may be permanently marked by the displaced fluid. The displaced fluid level may be calibrated to the intraocular pressure of the eyeball.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A tonometer comprising:

a) an eyepiece having a conduit extending through an outer surface, the outer surface being concave shaped to conform to an eyeball;

b) a plunger extending through the conduit having a head at a first end and having a probe at a second end which extends beyond the outer surface of the eyepiece so as to contact the eyeball when the eyepiece is positioned to conform to the eyeball;

c) a fluid reservoir having a top and a bottom, the bottom of the reservoir is sealed by a membrane that is in juxtaposition with the head of the plunger; and d) a breakable membrane positioned at the top of the reservoir for sealing the reservoir, the breakable membrane being adapted to receive an indicator for measuring a level of fluid in the reservoir, the level of fluid in the reservoir being proportional to an intraocular pressure of the eyeball when the eyepiece is positioned to conform to the eyeball.

2. The tonometer of claim 1 further comprising a fluid contained within the fluid reservior.

3. The tonometer of claim 2 wherein the fluid is a mineral oil or a gauge oil.

4. The tonometer of claim 1 further comprising a body for housing the membrane and reservoir, the body being coupled to the eyepiece.

5. The tonometer of claim 1 wherein the reservoir includes a plug for filling the reservoir with a fluid.

6. The tonometer of claim 1 wherein the reservoir further comprises an o-ring for sealing the bottom of the reservoir with the membrane.

7. The tonometer of claim 1 further comprising an indicator that is insertable into the breakable membrane.

8. The tonometer of claim 1 where the fluid reservoir is rigid.

9. A tonometer comprising:

a) a body;

b) an eyepiece coupled to the body having a conduit extending through an outer surface of the eyepiece, the outer surface being concave shaped to conform around an eyeball;

c) a plunger extending through the conduit having a head at a first end and having a probe at a second end which extends beyond the outer surface of the eyepiece so as to contact the eyeball when the eyepiece is positioned around the eyeball;

d) a fluid reservoir positioned within the body having a top and a bottom;

e) a membrane for sealing the bottom of the reservoir, the membrane is in juxtaposition with the head of the plunger; and f) an indicator positioned in the fluid reservoir and extending out of the body for measuring a level of fluid in the reservoir, the level of fluid in the reservoir being proportional to an intraocular pressure of the eyeball when the eyepiece is positioned around the eyeball.

10. The tonometer of claim 9 further comprising a fluid contained within the fluid reservoir.

11. The tonometer of claim 10 wherein the fluid is a mineral oil or a gauge oil.

12. The tonometer of claim 9 wherein the reservoir includes a plug for filling the reservoir with the fluid.

13. The tonometer of claim 9 further comprising an o-ring positioned within the body for sealing the bottom of the reservoir with the membrane.

14. The tonometer of claim 9 further comprising an indicator that is insertable into a breakable membrane prior to use.

15. A method of measuring intraocular pressure of an eyeball comprising:

(a) providing a fluid reservoir having a membrane for sealing a bottom of the reservoir, the membrane being in juxtaposition with a head of a plunger extending through an eyepiece;

(b) inserting an indicator into the fluid reservoir, the indicator extending out of a body for measuring a level of fluid in the reservoir;

(c) contacting the eyeball with the eyepiece;

(d) displacing the plunger a distance proportional to the force exerted on the plunger caused by contacting the eyeball to the eyepiece, the force being proportional to the intraocular pressure of the eyeball;

(e) displacing an amount of fluid proportional to the displacement of the plunger in step d and proportional to the intraocular pressure of the eyeball; and (f) measuring the fluid displacement in step e with the indicator, the displacement being proportional to the intraocular pressure of the eyeball.

16. The method of claim 15 wherein the step of contacting the eyeball with an eyepiece is performed with an eyelid of the eyeball closed.

17. The method of claim 15 further comprising the step of marking the indicator with the displaced fluid level.

* * * * *